(12) United States Patent
Mainusch et al.

(10) Patent No.: US 10,258,756 B2
(45) Date of Patent: Apr. 16, 2019

(54) ATRAUMATIC NASAL TUBE FOR NON-INVASIVE RESPIRATORY SUPPORT

(75) Inventors: Georg Mainusch, Koblenz (DE); Peter Schaller, Dresden (DE)

(73) Assignee: F. Stephen GmbH Medizintechnik, Gackenbach (DE)

( * ) Notice: Subject to any disclaimer, the term of this patent is extended or adjusted under 35 U.S.C. 154(b) by 501 days.

(21) Appl. No.: 13/259,824

(22) PCT Filed: Apr. 1, 2010

(86) PCT No.: PCT/DE2010/000381
§ 371 (c)(1),
(2), (4) Date: Sep. 23, 2011

(87) PCT Pub. No.: WO2010/112017
PCT Pub. Date: Oct. 7, 2010

(65) Prior Publication Data
US 2012/0017901 A1    Jan. 26, 2012

(30) Foreign Application Priority Data

Apr. 4, 2009  (DE) ................ 10 2009 016 150

(51) Int. Cl.
*A61M 16/06* (2006.01)
*A61M 16/08* (2006.01)

(52) U.S. Cl.
CPC ........ *A61M 16/0666* (2013.01); *A61M 16/06* (2013.01); *A61M 16/065* (2014.02); *A61M 16/0633* (2014.02); *A61M 16/0644* (2014.02); *A61M 16/0655* (2014.02); *A61M 16/0683* (2013.01); *A61M 16/0816* (2013.01); *A61M 2205/0238* (2013.01); *A61M 2210/0618* (2013.01)

(58) Field of Classification Search
CPC .......... A61M 16/0666; A61M 16/0633; A61M 16/06; A61M 16/0683; A61M 16/0644; A61M 16/0816; A61M 2210/0618
USPC ............ 128/204.18, 206.21, 206.27, 207.11, 128/207.13, 207.18
See application file for complete search history.

(56) References Cited

U.S. PATENT DOCUMENTS 2,259,817 A    10/1941  Hawkins
4,463,755 A *   8/1984  Suzuki ................. A61M 16/08
                                                128/200.18

(Continued)

FOREIGN PATENT DOCUMENTS

DE      19947722 A1   4/2001
WO    2004041341 A1   5/2004
WO    2008007985 A1   1/2008

*Primary Examiner* — Colin W Stuart
*Assistant Examiner* — Douglas Sul
(74) *Attorney, Agent, or Firm* — Lowe Graham Jones PLLC (57) ABSTRACT

An atraumatic nasal tube for non-invasive respiratory support (NIV-CPAP), having one central tube (5) extending from the nasal bridge, at a distance from the forehead area, to the nasal opening of the patient. The first end of the central tube (5) has an applicator (2) to be fixed to the forehead of the patient for connecting to a hose system coupled to a respiratory machine, and the second end of the central tube (5) comprises nasal connectors (6) protruding in a sickle shape out of the central tube (5) and opening into the nasal opening.

16 Claims, 8 Drawing Sheets

(56) References Cited

U.S. PATENT DOCUMENTS

| | | | | |
|---|---|---|---|---|
| 4,782,832 A | * | 11/1988 | Trimble | A61M 16/0666 128/204.18 |
| 5,042,478 A | * | 8/1991 | Kopala et al. | 128/207.18 |
| 5,134,995 A | * | 8/1992 | Gruenke | A61M 16/205 128/204.21 |
| 5,474,063 A | * | 12/1995 | Riendeau | 128/207.18 |
| 5,477,852 A | * | 12/1995 | Landis et al. | 128/207.18 |
| 5,687,715 A | * | 11/1997 | Landis et al. | 128/207.18 |
| 6,044,844 A | * | 4/2000 | Kwok et al. | 128/207.11 |
| 6,595,214 B1 | * | 7/2003 | Hecker et al. | 128/207.13 |
| 7,156,096 B2 | * | 1/2007 | Landis | A61M 16/06 128/204.18 |
| 7,357,136 B2 | * | 4/2008 | Ho et al. | 128/207.11 |
| 7,448,376 B2 | * | 11/2008 | Lepel | 128/200.14 |
| 7,665,465 B2 | * | 2/2010 | Radney | 128/207.11 |
| 7,905,232 B2 | * | 3/2011 | Olsen et al. | 128/207.18 |
| 8,161,971 B2 | * | 4/2012 | Jaffe | A61M 16/0666 128/206.11 |
| 2003/0047185 A1 | | 3/2003 | Olsen | |
| 2006/0174892 A1 | * | 8/2006 | Leksutin et al. | 128/207.11 |
| 2006/0283459 A1 | * | 12/2006 | Geiselhart | A61M 16/06 128/206.24 |
| 2007/0175480 A1 | * | 8/2007 | Gradon et al. | 128/207.11 |
| 2007/0240721 A1 | * | 10/2007 | Ho | A61M 16/06 128/207.13 |
| 2008/0053451 A1 | | 3/2008 | Bordewick | |
| 2009/0133697 A1 | * | 5/2009 | Kwok | A61M 16/0816 128/205.25 |
| 2010/0078026 A1 | * | 4/2010 | Andrieux | A61M 16/12 128/204.21 |

\* cited by examiner

ATRAUMATIC NASAL TUBE FOR NON-INVASIVE RESPIRATORY SUPPORT

BACKGROUND OF THE INVENTION

This is an application filed under 35 USC § 371 of PCT/DE2010/000381, filed on Apr. 1, 2010, claiming priority to DE 10 2009 016 150.3 filed on Apr. 4, 2009.

(1) Field of the Invention

The invention relates to an atraumatic nasal tube for non-invasive respiratory support (NIV-CPAP).

(2) Description of Related Art

In the field of mechanical ventilation or respiratory support those methods are referred to as non-invasive if the breathing gas is not supplied over an endotracheal tube penetrating into the body of the patient, a tracheal cannula or a tracheostoma, but over a nasal tube.

Such a nasal tube has two short nasal nozzles to be inserted into the nasal openings. Particularly in premature babies, due to the exceptional sensitivity of the columella and the nasal mucosa, after lengthy implantation periods of the nasal tube inflammations develop, in severe cases even necrotic changes in the nasal entrance area.

One cause, inter alia, is that all nasal tubes known in the state of the art have a tube oriented transverse to the columella, wherein the nasal nozzles exit from the transverse tube at an angle of 90° at a distance adapted to the thickness of the columella. In the worst case this transverse tube bears against the columella impairing blood circulation, which finally leads to columella necroses. This also leads to mucosa injuries in the interior of the nose, if the nasal nozzles are distanced too close or too far from each other. For that reason some manufacturers offer up to six different sizes in the neonatal area (newborns) in order to ensure optimal adaption to the geometric conditions of the nose.

BRIEF SUMMARY OF THE INVENTION

Therefore, the object of the invention is to propose an atraumatic nasal tube for non-invasive respiratory support which ensures great wearing comfort without occurrence of dermatitis or necroses, is easily adaptable to varying nasal septa and head shapes and can be produced at a reasonable cost.

According to the invention the atraumatic nasal tube for non-invasive respiratory support (NIV-CPAP) comprises at least one central tube which extends, at a distance to the nasal bridge, from the forehead area to the nasal opening of the patient. The first end of the central tube is provided with an applicator to be fixed to the forehead of the patient for connecting to a hose system which is coupled to a respiratory machine, and the second end of the central tube comprises nasal nozzles protruding in a sickle shape out of the central tube and opening into the nasal opening.

A significant advantage of the invention is that due to the sickle shaped design of the nasal nozzles and the absence of the transverse tube, compared with prior art, no component is placed directly opposite the columella so that the development of columella necroses is excluded by design. Further, the sickle shape is advantageous in that the nasal nozzles are more flexible due to their greater length, which reduces the forces applied to the nasal septum resulting in a reduced risk for the nasal mucosa. Also the curvature of the nasal nozzles brings about more flexibility so that greater differences in the thicknesses of the nasal septum are bridged, less different tube sizes being required.

The modular design of the nasal tube according to the invention, first, substantially simplifies manufacture. Second, worn parts can easily be replaced with new parts.

The applicator and hence indirectly also the central tube are fixed to the forehead of the patient preferably using a forehead support with the applicator in relation to the forehead support being adjustable longitudinally in direction of the nose bridge and/or at an angle to the forehead support.

The connection between the forehead support and the applicator can be established as a force-closed and/or form-closed mechanical connection or created by a magnetic force.

This mechanical connection allows a longitudinal and/or angular adjustment of the applicator in relation to the forehead support.

To establish a magnetic connection in case of longitudinal adjustment only the forehead support and the applicator each have a magnetic section established compatible to one another. It has shown to be particularly useful for practice, if the applicator is provided with a flat permanent magnet having a round cross-section and the forehead support is provided with a magnetic section in form of an oval, rectangle or ellipse that in the forehead region of the patient extends along the head median line of the patient so that a stepless height adjustment of the nasal tube for different face lengths can particularly easily be realized. The magnetic connection enables the nasal tube and forehead support to be very easily and quickly connected to each other.

The outside surface of the central tube is preferably established, at least partially, profiled with the profile in form of a corrugation extending in direction of the longitudinal axis of the central tube so that the nasal tube can more easily be deformed for the purpose of adapting it to the natural curvature of the upper half of the patient's face. To partially reduce the wall thickness of the central tube the corrugation can be established on the top or bottom side of the central tube. In selected applications the corrugation can extend annularly around the central tube.

The central tube preferably made of plastic preferably has as its cross-section an almost rectangular profile with rounded edges, with the ratio of width to height being about 2:1.

In a first preferred embodiment of the invention the central tube is provided with additional embedded metal strips, which for adapting the nasal tube to the natural curvature of the upper half of the patient's face, together with the corrugation extending in direction of the longitudinal axis of the central tube ensure that the central tube is reversibly deformable. These embedded metal strips are preferably located on the top side or the bottom side of the central tube, firmly connected to the central tube by material closure such as coated with plastic material. Instead of the flexible metal strips or sheets at least one wire core can be provided that preferably extend(s) within the walls of the faces of the central tube in the longitudinal direction of the central tube.

Another preferred embodiment of the invention abandons the fixation of the desired flexure of the central tube by means of metal strips or wire cores but provides an additional angular adjustment in the applicator so that also the inclination of the central tube in relation to the forehead support can be modified. This solution is advantageous in that both the distance and the inclination of the nasal tube according to the invention can be optimally adapted to the geometric conditions between forehead support and nose entrance area. The high flexibility of the central tube substantially reduces all force effects caused by the respiratory hoses on the nares.

For an even better fixation of the nasal nozzles to the nares a clamp is provided placed on the second end of the central tube by form closure. This clamp comprises fixation possibilities for additional bands which, for example, coming from the forehead support fix the central tube also in horizontal direction.

The applicator comprises several coupling connectors for feeding and removing mediums such as a coupling connector for the inflowing inspiration gas, a coupling connector for the outflowing expiration gas and a coupling connector, closed by a cap, for a pressure measuring device. Each of said coupling connectors, depending on the demand, is preferably coupled to a hose, the hoses connected to a respiratory machine.

Supply of drugs through the nasal tube according to the invention is preferably performed using a connector, or a drug connector, respectively, that is realised by slipping an adaptor over the hose of the inspiration branch. The drugs are dosed as required. Optionally also the applicator can comprise such a connector.

For the purposes of the length adjustment of the nasal tube and of the connection between central tube and applicator the first end of the central tube and the coupling connector for the central tube of the applicator are established as joining partners slideable within each other with the internal contour of the first end of the central tube and the external contour of the associated coupling connector of the applicator established complementary to each other. In other words, the applicator can manually be slipped on the associated coupling connector of the central tube. The connections to the inspiratory and expiratory hoses are made using the other coupling connectors.

In the central tube of the atraumatic nasal tube of the invention a partition arranged median is placed extending in direction of the longitudinal axis of the nasal tube, dividing the central tube into a first flow chamber for the inspiration gas and a second flow chamber for the expiration gas. This partition, which prevents the inspiration and expiration gases from mixing early, extends starting from the first end of the central tube, i. e. directly between the coupling connector for the inspiration gas and the coupling connector for the expiration gas, up to about 5 to 15 mm before the second end of the central tube, ending there. But the partition is disadvantageous in that it increases the stiffness of the nasal tube against a desired bending. In order to avoid this penalty the partition, in an alternative embodiment, is established partly interrupted or consisting of several webs distanced from each other at their faces. As shown in extensive series of measurement, with the geometric conditions of the central tube and the chosen volume flows no $CO_2$-rebreathing is expected so that in a particularly simple embodiment of the invention the partition can be totally dispensed with.

The nasal nozzles are preferably provided with annular reductions of the wall thickness. These annular reductions of the wall thickness contribute to making the nasal nozzles more flexible.

The nasal nozzles can be designed to have a circular profile or, preferably, a triangular profile adapted to the shape of the nares. Use of a triangular profile results in a larger outlet cross-section, with a lower flow resistance and better sealness against the nasal septum.

In an advantageous embodiment of the invention the internal cross-section of the nasal nozzles reduces starting from the central tube up to the outlet placed in the nose opening. This prevents the flow resistance from increasing due to the greater length of the nasal nozzles.

Further, it is possible to provide a clip fastening device in the area of the second end of the central tube as device for angular adjustment, which also serves to adjust the inclination of the central tube in relation to the forehead support.

The significant advantages of the invention over the state-of-the art essentially are:

The nasal tube modularly established of only a small number of components is manufacturable cost-efficiently and easy to mount;

Due to the sickle shape design of the nasal nozzles and non-existence of the transverse tube of the nasal tube of prior art no component is directly opposite to the columella so that development of columella necroses is excluded by design;

Based on the magnetic section of the forehead support of the patient, with the magnetic section extending along the head median line of the patient, a stepless height adjustment of the nasal tube to adapt to different face lengths can particularly easily be realised;

The optional possibility of an angular adjustment enables the nasal tube to be adapted to a large degree to the geometry of the face also in relation to the angle;

The nasal tube is usable with various respiratory systems by using its applicator provided with several coupling connectors;

By means of the corrugation that extends in direction of the longitudinal axis of the central tube and/or the embedded wire cores the nasal tube can be elastically deformed to be adapted to the natural curvature of the upper half of the patient's face;

The applicator is optionally provided with an additional coupling connector, or an interface, respectively, for drugs;

By use of profiles with triangular cross-section a larger outlet cross-section leading to lower flow resistance and better sealness against the nasal septum is achieved;

The nasal tube is optionally provided with a clip fastening device in the area of the central tube or applicator in order to make possible to use it also with agile babies.

BRIEF DESCRIPTION OF THE DRAWINGS

The objects and advantages of the present invention will become apparent from consideration of the following detailed description of the here preferred, not limiting exemplary embodiments of the invention when taken in connection with the accompanying drawings, of which show:

FIGS. 6.1 to 6.3: a forehead support in various views; and

DETAILED DESCRIPTION OF THE INVENTION

Figure 1:
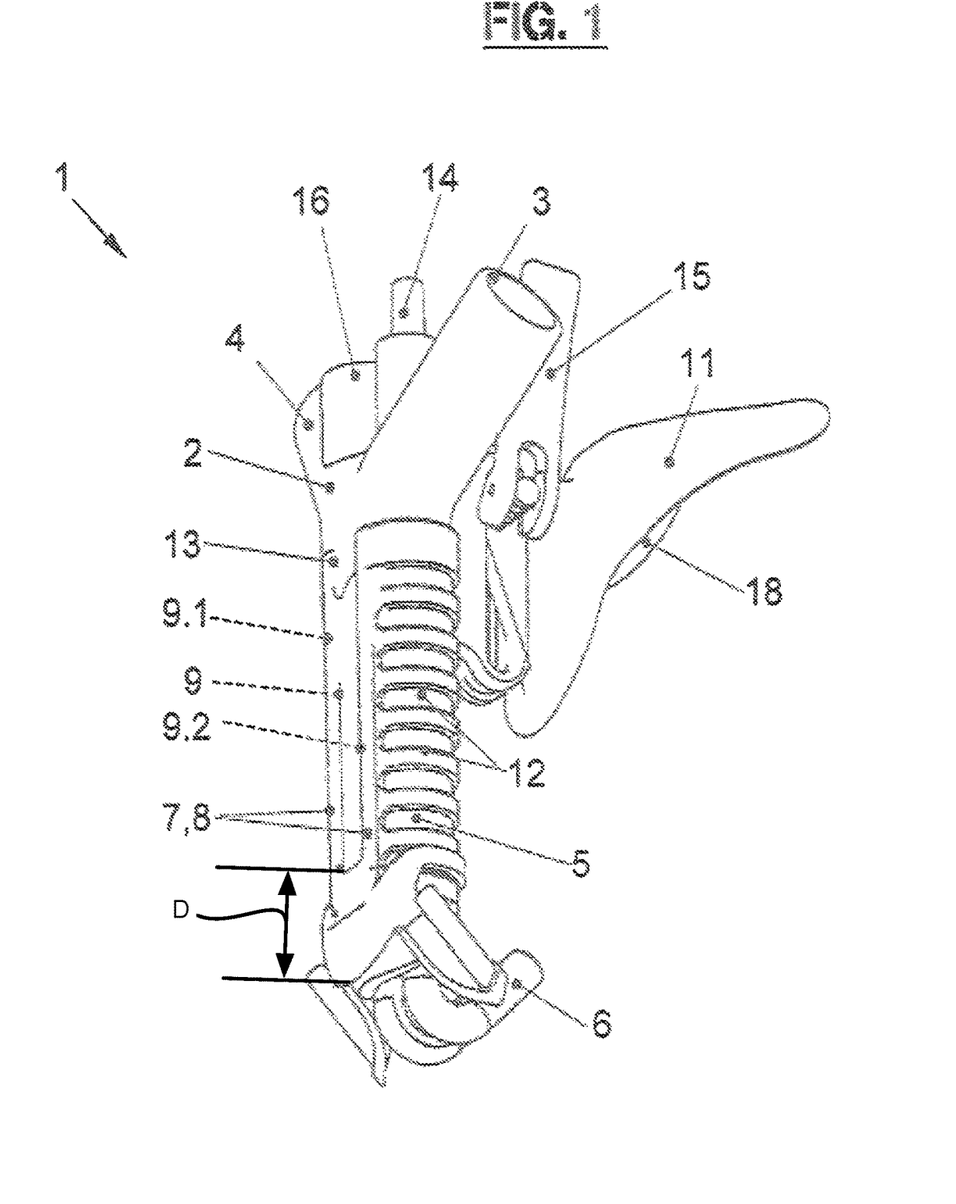
FIG. 1: a perspective representation of the nasal tube with clip fastening device for angular adjustment as complete system.
Figure 7:
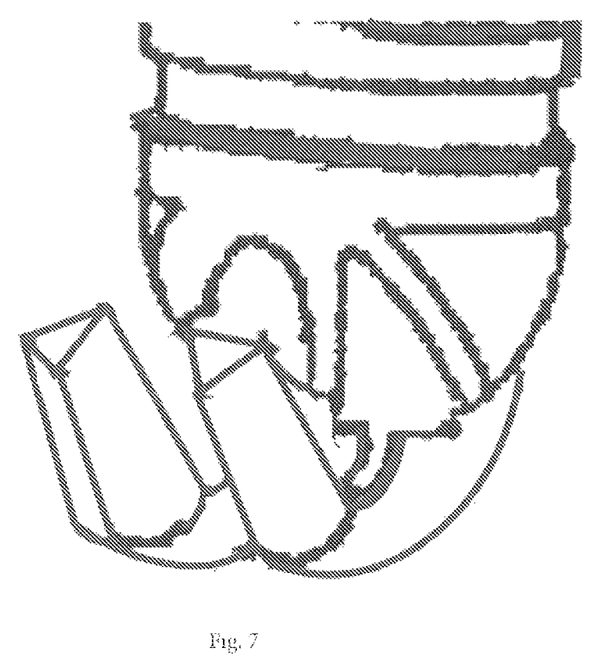
FIG. 7: an isometric view of a nasal tube having a triangular cross section.
Figure 61:
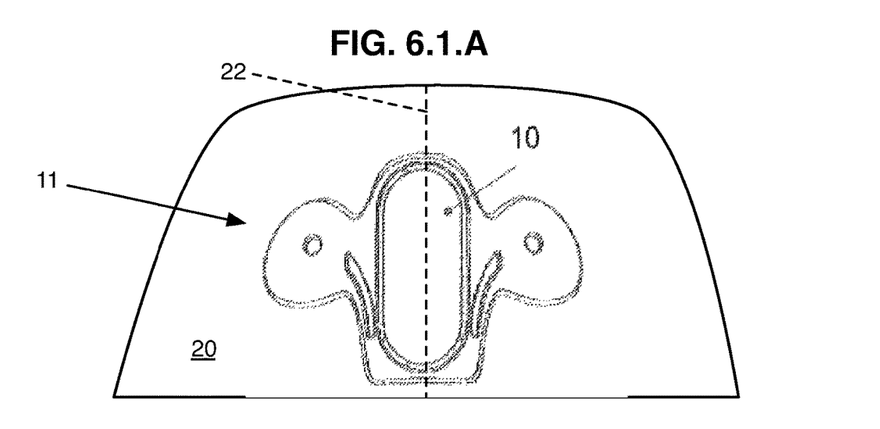
Figure 62:
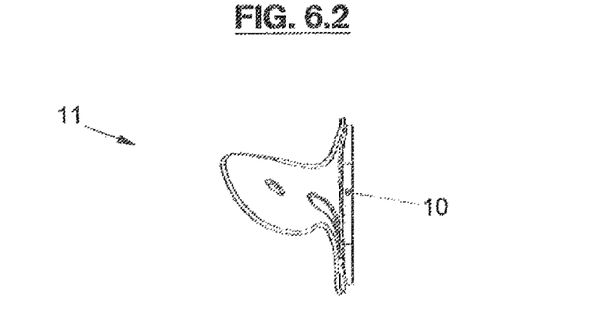
Figure 63:
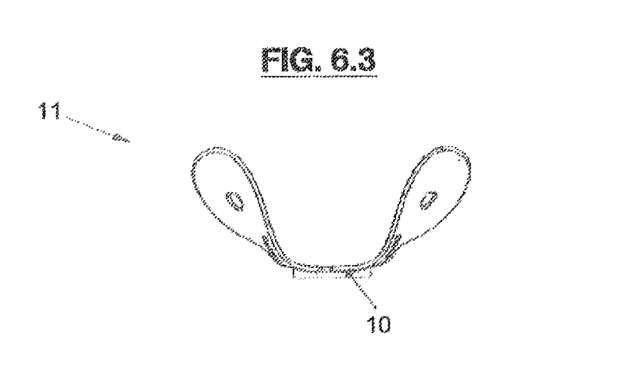

FIG. 1 illustrates an atraumatic nasal tube 1 for non-invasive respiratory support (NIV-CPAP) with additional angular adjustment in a perspective representation. In the example shown the nasal tube 1 comprises a central tube 5 that extends, at a distance to the nose bridge, from the forehead area to the nasal opening of the patient, wherein the first end of the central tube is provided with an applicator to be fixed to the forehead of the patient for connecting to a hose system which is coupled to a respiratory machine, and the second end of the central tube comprises nasal nozzles 6 which protrude in a sickle shape out of the central tube 5 and open into the nasal opening. The applicator 2 is provided with a coupling connector 3 for the inflowing inspiration gas, a coupling connector 14 for the central tube 5 and two coupling connectors 13 for drugs to be supplied. For the purposes of length adjustment of the nasal tube 1 and for coupling the first end of the central tube 5 and the coupling connector 14 for the central tube 5 of the applicator 2 are established as joining partners slideable within each other, with the internal contour of the first end of the central tube 5 and the external contour of the coupling connector 14 of the applicator 2 established complementary to each other. The outside surface of the central tube 5 is established, least partially, profiled with the profile extending in form a corrugation 12 in direction of the longitudinal axis of the central tube 5. This corrugation 12 comprises material enlargements and recesses, respectively, extending transverse to the longitudinal axis of the central tube 5. Therefore, the elasticity of the central tube 5 is further increased in excess of that due to the flexible plastic material the central tube 5 is made of so that the nasal tube 1 can optimally be adapted to the natural curvature of the upper half of the patient's face. Within the central tube 5 a partition 9 arranged median is placed that divides the central tube 5 into a first flow chamber 9.1 for the inspiration gas and a second flow chamber 9.2 for the expiration gas. This partition 9 ends about 5 to 15 mm before the second end of the central tube 5 (see distance D). The two nasal nozzles 6 exiting from the central tube 5 in a sickle shape manner each are provided with a triangular profile adapted to the shape of the nares (see FIG. 7). The internal cross-section of the nasal nozzles 6 reduces starting from the central tube 5 up to the outlet placed in the nose opening. Both nasal nozzles 6 essentially run parallel to each other, extending—with the nasal tube applied to the patient—starting from the second end of the central tube 5 over the tip of the nose up to the nose openings. The central tube 5 is established having a largely rectangular cross-section with rounded with the ratio of width to height being about 2:1. In the area of the narrow faces of the central tube 5, on each side, a wire core is embedded, or coated with plastics, respectively, in order to give the central tube 5 a reversible deformation potential for adapting to the curvature of differently established upper halves of the patients. In the area of the applicator 2 a clip fastening device 15 is placed that enables, on the one hand, to realize the length adjustment of the nasal tube 1 to the face length and, on the other hand, the inclination of the nasal tube 1 for adapting to the curvature of the patient's face.

Figure 2:
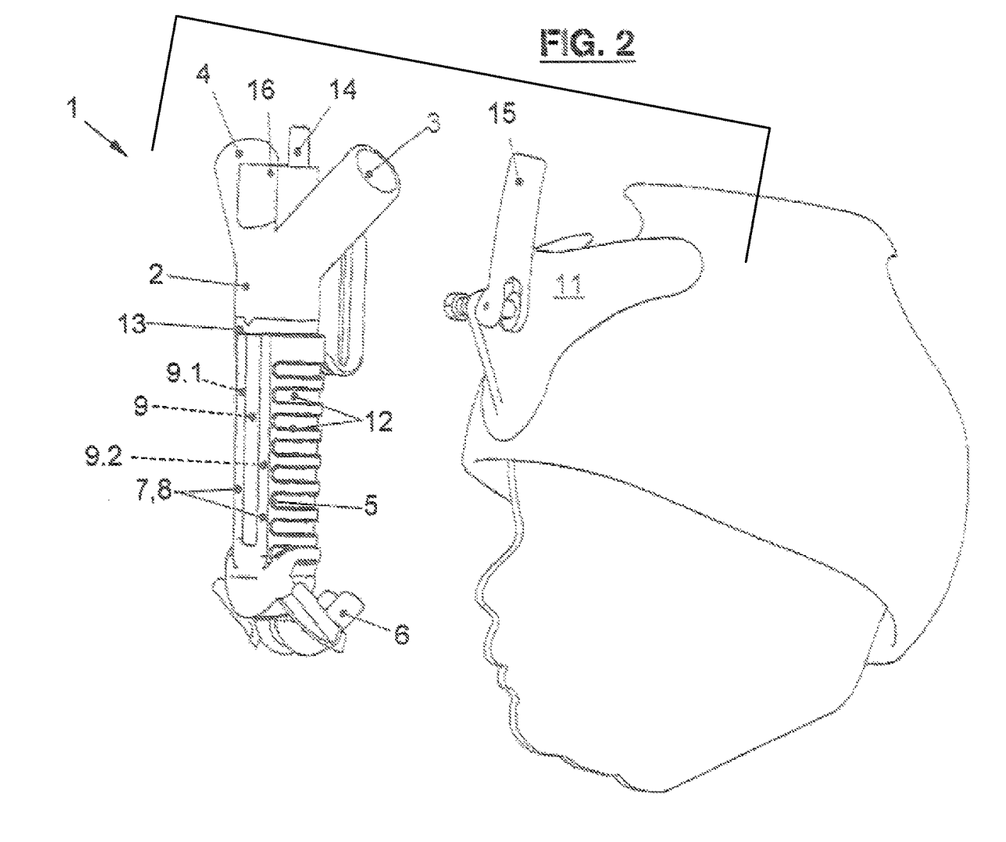
FIG. 2: a perspective representation of the nasal tube with clip fastening device for angular adjustment and additional forehead support immediately before mounting.

FIG. 2 shows a perspective representation of the nasal tube and the forehead support immediately before mounting with the forehead support placed on an indicated medical cap which arrests the forehead support 11 indirectly to the head of the patient. Instead of the cap, optionally, a band with a velcro closure can be used, the band tigthened around the patient's head. The forehead support 11 serves to fix the applicator 2, hence the nasal tube 1, to the forehead of the patient by use of said band or a velcro closure 18. The velcro closure 18 establishes a first fixation point of the nasal tube 1. The second fixation point is obtained by the nasal nozzles 6 exiting in a sickle shape from the central tube 5, ending in the nose openings, according to FIGS. 3 and 4.

Figure 3:
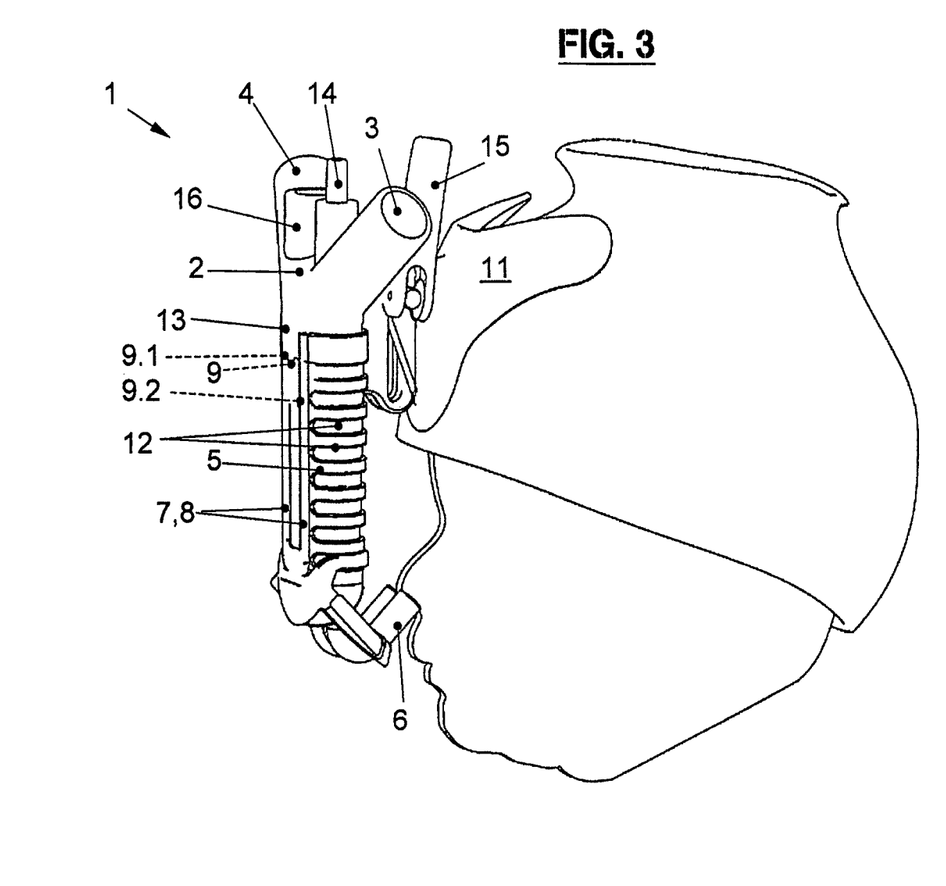
FIG. 3: a perspective representation of the nasal tube with clip fastening device for angular adjustment in combined action with the forehead support while used for respiratory support.

In FIG. 3 a perspective representation of the nasal tube 1 in combined action with the forehead support 11 is shown while used for respiratory support. As seen, the nasal tube 1 according to the invention extends starting from the forehead up to the nose opening of the patient. The nasal tube 1 is particularly advantageously provided with only two fixation points at the patient, a first fixation point in the area of the applicator 2 that is placed at the first end of the central tube 5, and a second fixation point established at the second end of the central tube 5 in form of both nasal nozzles 6. Except the nasal nozzles 6 ending in the nose openings, no component of the nasal tube 1 according to the invention directly contacts the unprotected skin in the area of the patient's nose entrance. This effectively prevents tender spots and necroses. The nasal tube 1 arranged, nevertheless, very close to the head of the patient, can be set into the desired position in a few easy steps and easily adapted to the various face shapes by length adjustment and adjustment of the curvature of the central tube 5.

In all the FIGS. 1 to 3 described above the nasal tube 1 comprises a clip fastening device 15 as angular adjustment device, by use of which also the inclination of the central tube 5 in relation to the forehead support 11 can be changed. This solution is advantageous in that both the distance and the inclination of the nasal tube 1 can be optimally adapted to the geometric conditions between the forehead support 11 and nose entrance area. The high flexibility of the central tube 5 substantially reduces all force effects on the nares caused by the not-shown respiratory hoses. For an even better fixation of the nasal nozzles 6 to the nares a clamp is provided placed on the second end of the central tube 5 by form closure. This clamp comprises fixation possibilities for additional bands which, for example, coming from the forehead support fix the central tube 5 also in horizontal direction.

Figure 4:
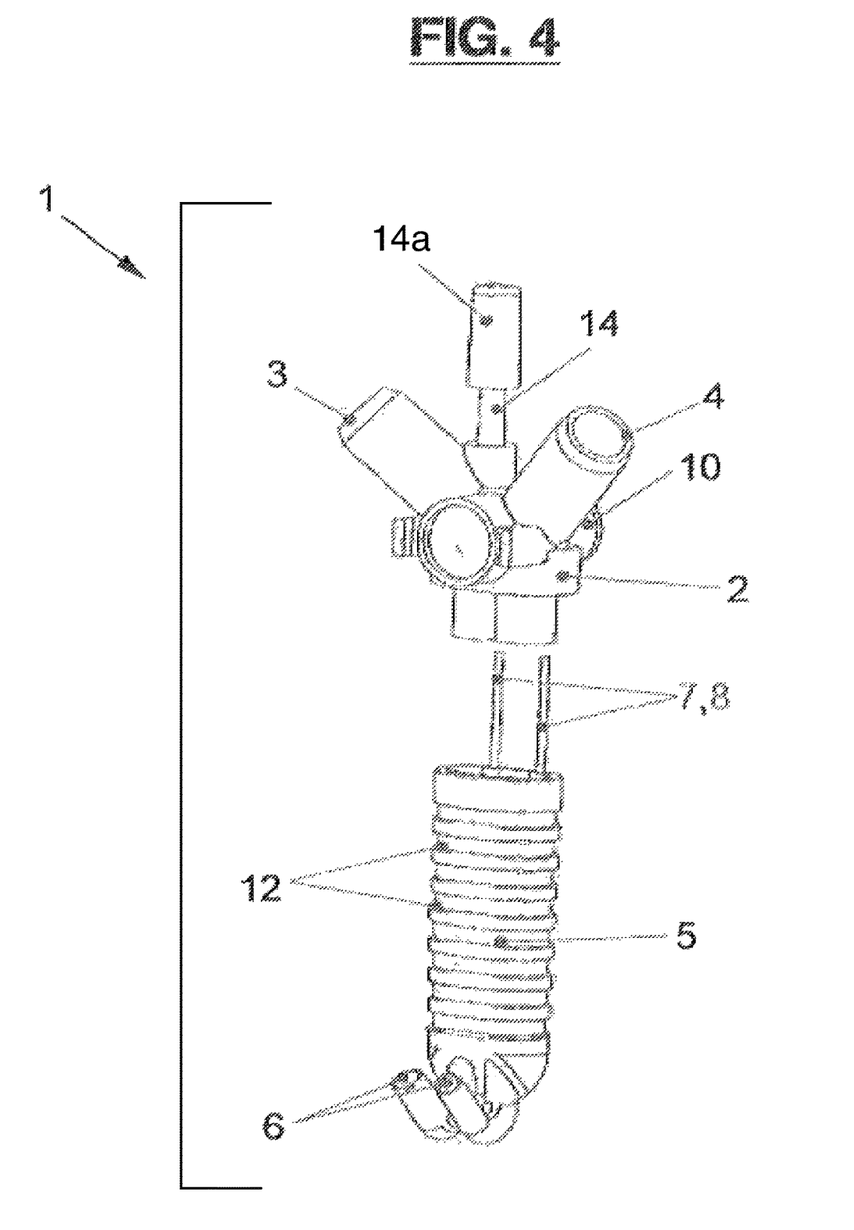
FIG. 4: a perspective representation of the nasal tube with magnetic adjustment as complete system.

FIG. 4 shows a perspective representation of the nasal tube 1 with magnetic adjustment as complete system. The nasal tube 1 essentially corresponds to the nasal tube 1 as described in the FIGS. 1 to 3 with the difference that here the metal strips 7, or wire cores 8, respectively, placed in the central tube 5 are seen. Here, the metal strips 7, or wire cores 8, respectively, established in pairs extend in direction of the longitudinal axis of the central tube 5. Another major difference to the embodiment described above consists in that in the example of embodiment to FIG. 4 the forehead support 11 does not comprise a clip fastening device 15 for angular adjustment. Rather, a magnetic connection is used that fixes the applicator 2 to the forehead support 11. The magnetic connection is established by a circular magnetic section 10 that is compatible to the magnetic section of the forehead support 11 to the FIGS. 6.1A to 6.3. The magnetic section 10 of the forehead support 11 and the magnetic section 10 of the applicator 2 as a magnetic connection establish a first fixation point of the nasal tube 1. In an of the invention the magnetic section 10 of the forehead support 11 is established as oval (FIG. 6.1.A), rectangle (FIG. 6.1.B) or ellipse (FIG. 6.1.C) that in the forehead region 20 of the patient extends along the head median line 22 of the patient so that a stepless height adjustment of the nasal tube 1 for different face lengths can he realised.

Figure 5:
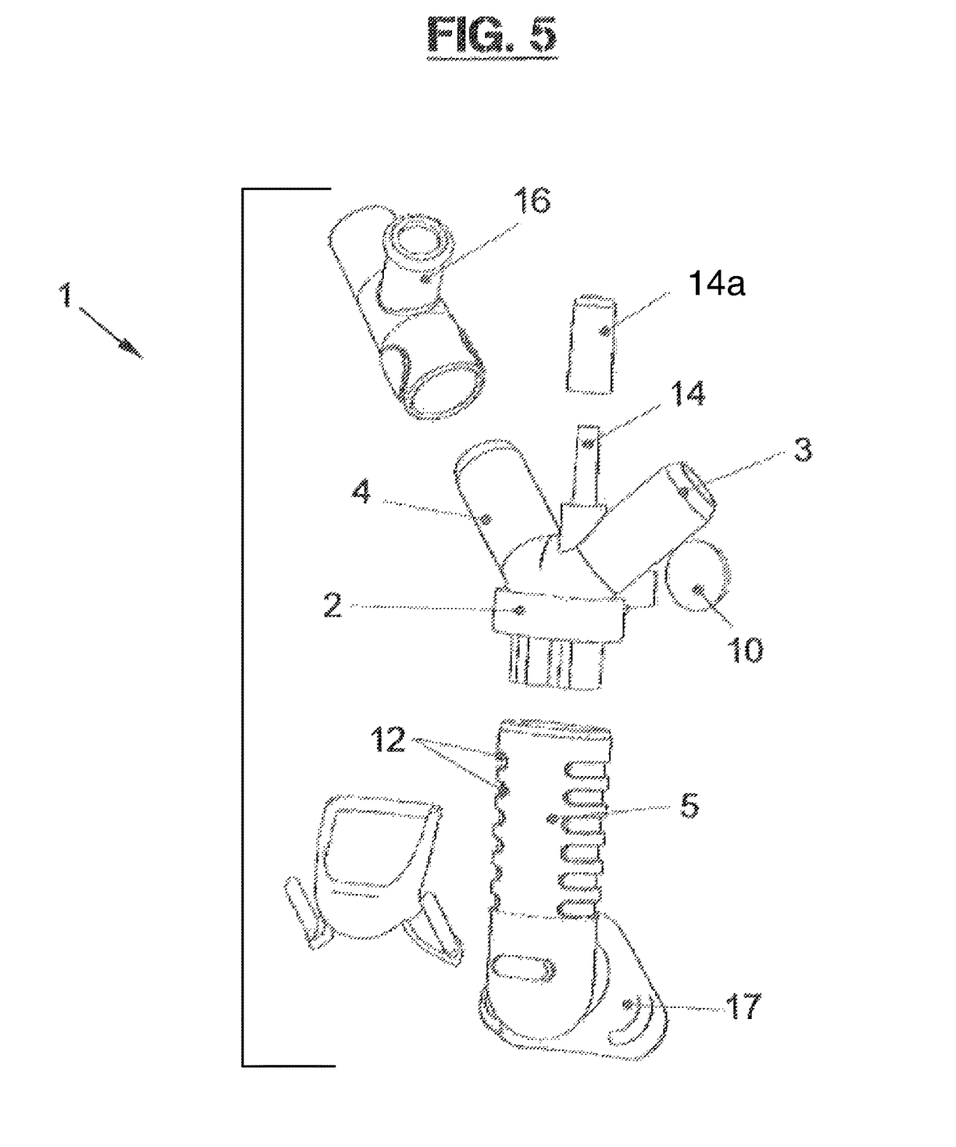
FIG. 5: an explosive representation of the nasal tube and mask.

FIG. 5 shows an explosive representation of the nasal tube 1. The essential features of the nasal tube 1 shown here are the flexible mask 17 placed at the second end of the central tube 5, inserted instead of the sickle shaped nasal nozzles 6, and the coupling connector 16 for drug supply, which is not placed immediately at the applicator 2 but at an adaptor piece in the inspiratory branch, or inspiration hose, respectively. The mask 17 is—just as the nasal nozzles 6 are—directly connected to the central tube 5 so that in view of assembly when using this mask 17 only the central tube 5 has to be replaced where the desired components, that is the mask 17 or the nasal nozzles 6, are optionally placed. These two different embodiments can clearly be seen when comparing FIGS. 4 and 5.

FIGS. 6.1 to 6.3 illustrate a forehead support 11 in various views. The forehead support 11 placed on a head bonnet or head cap is largely established in a butterfly shape, with both wings curved corresponding to the patient's head shape. The curvature is obtained by that the forehead support 11 is established to be of plastic material. Between both wings an oval magnetic section 10 is located that corresponds to the magnetic section 10 of the applicator 2 to FIG. 5, so that the applicator 2 is magnetically held to the forehead support 11. Due to the oval design of the magnetic section 10 the nasal tube 1 can particularly easily be adapted to the length of the patient's face. Further, the wings each comprise a velcro closure that is arrested at a cap to be placed on the patient's head, or a headband, respectively.

NOMENCLATURE 1 nasal tube
2 applicator
3 coupling connector for the inspiration hose
4 coupling connector for the expiration hose
5 central tube
6 nasal nozzle
7 metal strip
8 wire core
9 partition
9.1 first flow chamber
9.2 second flow chamber
10 magnetic section
11 forehead support
12 corrugation
13 cap for pressure measuring connector
14 coupling connector for pressure measuring device
15 clip fastening device
16 coupling connector for drug supply
17. mask
13 a coupling connectors for drugs
14a cap for pressure measuring connector

The invention claimed is:

1. An atraumatic nasal tube (1) for non-invasive respiratory support (NIV-CPAP), comprising
  a central tube (5) configured to pass inspiration and expiration gases, the central tube configured to extend along a nasal bridge from a forehead area to a nasal opening of a patient, with a first end of the central tube (5) provided with an applicator (2) configured to be fixed to the forehead area of the patient for connecting to a hose system which is coupled to a respiratory machine, and a second end of the central tube (5) comprising nasal nozzles (6) protruding in a sickle shape out of the central tube (5) and having nozzle openings configured to open into the nasal opening, in that no component bears against the columella;
  wherein no partition preventing the inspiration and expiration gas from mixing is present in the central tube;
  wherein the applicator (2) comprises a plurality of coupling connectors (3, 4, 13, 14, 16) comprising a coupling connector (3) for inflowing inspiration gas and a coupling connector (4) for outflowing expiration gas, the coupling connectors for inflowing inspiration gas and outflowing expiration gas being the same size;
  wherein the applicator (2) is fixed to a forehead support (11) magnetically, with the forehead support (11) and the applicator (2) each comprising a magnetic section (10), the magnetic sections being compatible to each other;
  wherein the magnetic section (10) of the forehead support (11) is established as oval, ellipse or rectangle, which in the forehead area of the patient extends along a head median line of the patient effective to achieve a stepless height adjustment of the nasal tube (1) for different face lengths;
  wherein the coupling connector (3) for inflowing inspiration gas defines an inspiration channel and the coupling connector (4) for outflowing expiration gas defines an expiration channel, the inspiration and expiration channels having a same size;
  wherein the central tube defines a tube channel from the applicator to the nasal nozzles such that there are no openings other than the nozzle openings in a fluid path from the applicator to the nozzle openings, the tube channel being in fluid communication with both the inspiration channel and expiration channel.

2. The atraumatic nasal tube (1) according to claim 1, wherein the applicator (2) is configured to affix to the patient's forehead using a forehead support (11), with the applicator (2) in relation to the forehead support (11) being adjustable at least one of longitudinally in direction of the nose bridge of the patient and angularly.

3. The atraumatic nasal tube (1) according to claim 1, wherein the plurality of coupling connectors (3, 4, 13, 14, 16) are configured to perform feeding and removing media, the plurality of coupling connectors selected from a group consisting of further comprising a coupling connector for the central tube (5), a coupling connector (14) for a pressure measuring device and a coupling connector (16) for the supply of drugs.

4. The atraumatic nasal tube (1) according to claim 1, wherein each of the nasal nozzles (6), include a first portion extending downwardly from the central tube and a second portion secured to a distal end the first portion and extending upwardly from the first portion.

5. The atraumatic nasal tube (1) according to claim 4, wherein the nasal nozzles (6) protrude downwardly from a downward facing surface defined at a lower end of the central tube.

6. The atraumatic nasal tube (1) according to claim 5, wherein the nasal nozzles (6) are parallel to one another.

7. The atraumatic nasal tube of claim 1, wherein the applicator is provided with a magnet having a round cross section.

8. The atraumatic nasal tube of claim 1, wherein the central tube has as a cross section thereof an approximately rectangular profile with rounded edges and a ratio of height to width of approximately two to one.

9. The atraumatic nasal tube of claim 1, wherein the central tube comprises one or more embedded metal strips configured to enable adapting the central tube to a natural curvature of an upper half of the patient's face, the central tube being corrugated in a direction of a longitudinal axis of the central tube such that the central tube is reversibly deformable.

10. The atraumatic tube of claim 1, further comprising at least one wire core extending within walls of the central tube in a direction of a longitudinal axis of the central tube.

11. The atraumatic nasal tube of claim 1, wherein the central tube is adapted to extend to a tip of a nose of the patient.

12. The atraumatic nasal tube of claim 1, wherein an angular adjustment in the applicator is provided such that inclination of the central tube in relation to the applicator are modifiable in that both a distance and the inclination of the central tube are adjustable to geometric conditions between the applicator and the nasal opening of the patient.

13. The atraumatic nasal tube of claim 1, wherein the nasal nozzles are configured to have a triangular profile adapted to a shape of nares of the patient.

14. The atraumatic nasal tube of claim 13, wherein an internal cross-section of the nasal nozzles reduces starting from a point of attachment of the nasal nozzles to the central tube up to an outlet end of the nasal nozzles positionable in the nasal openings of the patient.

15. The atraumatic nasal tube of claim 1, wherein the central tube (5) configured to pass inspiration and expiration gases is flexible.

16. The atraumatic nasal tube of claim 1, wherein the nasal nozzles (6) protruding in a sickle shape out of the central tube (5) are flexible.

\* \* \* \* \*